United States Patent [19]

Ulrich et al.

[11] Patent Number: 5,084,481

[45] Date of Patent: Jan. 28, 1992

[54] METHOD OF TREATING INFLAMMATORY DISEASES WITH PHARMACEUTICAL COMPOSITION CONTAINING DIHYDROLIPOIC ACID AS ACTIVE SUBSTANCE

[75] Inventors: Heinz Ulrich, Niedernberg; Carl-Heinrich Weischer, Bonn; Jürgen Engel, Alzenau; Helmut Hettche, Dietzenbach, all of Fed. Rep. of Germany

[73] Assignee: Asta Pharma Aktiengesellschaft, Fed. Rep. of Germany

[21] Appl. No.: 476,042

[22] Filed: Feb. 8, 1990

[30] Foreign Application Priority Data

Feb. 9, 1989 [DE] Fed. Rep. of Germany ....... 3903758

[51] Int. Cl.⁵ ..................... A61K 31/19; A61K 31/20; A61K 31/095
[52] U.S. Cl. ................................. 514/557; 514/558; 514/706; 514/886; 514/440
[58] Field of Search ............... 514/557, 558, 706, 724, 514/886

[56] References Cited

U.S. PATENT DOCUMENTS 2,933,430 4/1960 Rosenberg ............................ 167/53

FOREIGN PATENT DOCUMENTS 0002219 6/1979 European Pat. Off. ............ 514/557

0318891 6/1989 European Pat. Off. .

OTHER PUBLICATIONS

N. Kurihara and K. Shibata: Effect of Thiol-Compound on Toxicity of Habu Snake (Trimeresurus Flavoviridis Hallowell) Venom, Japan. J. Pharmacol. 21, 253-261 (1971).

Y. Sawai et al.: Studies on the Improvement of Treatment of Habu (Trimeresurus Flavoviridus) Bites, 7. Experimental Studies on the Habu Venom Toxoid by Dihydrothioctic Acid, Japan, J. Exp. Med. vol. 29, 2, 109-117 (1969).

Y. Saivai et al.: Studies on the Inactivation of Snake Venoms by Dihydrothioctic Acid, Japan. J. Exp. Med. vol. 37, 121-128 (1967).

R. Tirrell et al.: The Fate of Proteinases of Mamushi Venom during Preparation of Toxoid, Japan. J. Exp. Med. vol. 44, 13-17 (1974).

*Primary Examiner*—Frederick E. Waddell
*Assistant Examiner*—Kimberly R. Jordan
*Attorney, Agent, or Firm*—Cushman, Darby & Cushman

[57] ABSTRACT

Pharmaceutical compositions and their preparation which contain dihydrolipoic acid or its pharmaceutically acceptable salts as active substance. The pharmaceutical compositions have a cytoprotective effect and are suitable for combatting pain and inflammatory disorders.

2 Claims, No Drawings

METHOD OF TREATING INFLAMMATORY DISEASES WITH PHARMACEUTICAL COMPOSITION CONTAINING DIHYDROLIPOIC ACID AS ACTIVE SUBSTANCE

The present invention relates to pharmaceutical compositions which contain, as active ingredient, dihydrolipoic acid or a pharmaceutically acceptable salt of dihydrolipoic acid. The invention also relates to the preparation of such compositions as well as the use of the dihydrolipoic acid or its salts for the preparation of pharmaceutical compositions.

BACKGROUND OF THE INVENTION

Dihydrolipoic acid is 6,8-dimercapto-octanoic acid. Animal experiments have shown that dihydrolipoic acid inactivates snake venom. These investigations have, for example, been carried out in rats and mice using solutions in water or physiological sodium chloride solution containing the snake venom and dihydrolipoic acid.

SUMMARY OF THE INVENTION

It is an object of the invention to provide improved pharmaceutical compositions having, for example, analgesic, anti-inflammatory and cytoprotective effects. These and other objects are provided in pharmaceutical compositions which contain, as active ingredient, dihydrolipoic acid or a pharmaceutically acceptable salt of dihydrolipoic acid. The present invention also provides a method for the preparation of such compositions as well as for the use of the dihydrolipoic acid or its salts for the preparation of pharmaceutical compositions. These compositions have, in particular, a cytoprotective effect and are, in addition, suitable for combatting pain and inflammatory disorders.

The amounts per weight set out in the claims relate, in each case, to pure dihydrolipoic acid and not to the salts. When salts are used, the amounts must be adjusted accordingly, to take into account the difference between the molecular weight of pure dihydrolipoic acid and the molecular weight of the salt.

The dihydrolipoic acid is preferably used as a free acid, in aqueous solutions to form the salt with pharmaceutically acceptable salt forming substances.

Dihydrolipoic acid may be used as a racemate or in the form of the two optical isomers (R(+) and S(−) form).

Dihydrolipoic acid displays a good analgesic effect in for example the acetic acid writhing pain test in mouse and in the Randall Selitto inflammation pain test in rat. The effect is superior to that of alpha-lipoic acid by a factor of at least 1.9 and 2.8 respectively (peroral application).

In addition, dihydrolipoic acid displays a good anti-inflammatory activity for example in carragheen-induced edema in the rat which is also superior to that of alpha-lipoic acid by a factor of at least 1.9 (peroral application). Dihydrolipoic acid also displays good inhibition of vasopermeability for example in PAF edema in the rat as well as a good cytoprotective effect.

Thus, for example, in the above mentioned acetic acid writhing test dihydrolipoic acid produces an analgesically effective $ED_{50}$ at 26.8 mg/kg given per os and 4.6 mg/kg given intraperitoneally.

In the above mentioned Randall Selitto test, dihydrolipoic acid produces an analgesically effective $ED_{50}$ at 16.2 mg/kg given per os and 0.14 mg/kg given intraperitoneally.

In the above described carragheen edema test, dihydrolipoic acid produces for example an anti-inflammatorily effective $ED_{50}$ of 26 mg/kg per os and 7.7 mg/kg intraperitoneally.

The minimum dose to produce an analgesically effect in the Randall Selitto pain test is for example 5 mg/kg per os.

The minimum dose to produce an anti-inflammatory effect in the carragheen-induced edema test is for example 5 mg/kg per os.

Similarly, the cytoprotective effect in animal trials occurs at doses of 5 mg/kg per os.

The general dose range that may be considered for the analgesic effect is for example 5-100 mg/kg given orally The general dose range that may be considered for the anti-inflammatory and cytoprotective effect is for example 5-100 mg/kg given orally The effect of dihydrolipoic acid is set out in the following table:

| Experimental model | $ED_{50}$ mg/kg | | % effect |
|---|---|---|---|
| Carragheen edema | 26 | per os | |
| | 7.7 | intraperitoneally | |
| Randall Selitto | 16.2 | per os | |
| Inflammatory pain | 0.14 | intraperitoneally | |
| Acetic acid | 26.8 | per os | |
| writhing test | 4.6 | intraperitoneally | |
| PAF-acether edema | 25 mg/kg | intraperitoneally | 14% |
| | 50 mg/kg | intraperitoneally | 63% |
| | 200 mg/kg | intraperitoneally | 73% |

In addition, dihydrolipoic acid displays a good analgesic, anti-inflammatory, anti-arthrotic and cytoprotective effect in the following investigatory models:

$MgSO_4$ writhing test in the mouse after GYIRES et al. (Arch. int. pharmacodyn. therap. 267, 131-140, 1984)

Adjuvans arthritis in the rat after NEWBOULD (Brit. J. Pharmacol. 21, 127-136, 1963)

TPA or arachidonic acid-induced mouse ear edema after YOUNG et al. (J. Invest. Dermatol. 80, 48-52, 1983)

Na-mono-iodine acetate-induced arthrosis in rats or chickens after KALBHEN, in: Arthrosis deformans, Eular-Verlag, Basel/Switzerland, 1982

TPA-induced arthrosis in rats after WEISCHER (Agents and Actions 23, ½, 1988)

Intestinal ulceration in rats after DEL SOLDATO (Agents and Actions 16, 393-396, 1985)

Colitis model in the rat after WEISCHER (Agents and Actions, 1988)

Ethanol ulcer model in the rat (determination of, for example, a cytoprotective effect)

The effect of topical DL-dihydrolipoic acid in the complex of symptoms induced by UV-B radiation in healthy subjects Dihydrolipoic acid inhibits for example acute inflammation and inflammatory pain. It is, for example, also suitable for treating inflammations of the vessels and vascular connective tissue, such as in arteriosclerosis, etc.

Dihydrolipoic acid has a specific cytoprotective effect.

Indications for human patients that may for example be considered are: inflammatory, degenerative articular and extra-articular rheumatic disorders, non-rheumatic inflammatory and swollen states, Arthrosis deformans, chrondropathies, periarthritis, inflammatory and non-inflammatory disorders of the skin such as for example neurodermatitis and psoriasis, inflammatory and non-inflammatory disorders of the gastrointestinal tract such as for example gastritis, Ulcus ventriculi, ileitis, duodenitis, jejunitis, colitis, polyneuropathy of diabetic, alcoholic, hepatic and uraemic origin, liver parenchyme degeneration, hepatitis, fatty liver and fatty cirrhosis as well as chronic liver disorders, inflammatory respiratory tract disorders, for example Asthma bronchiale, sarcoidosis, ARDS (acute respiratory distress syndrome).

The daily doses of the dosage forms of the invention to produce an analgesic, cytoprotective and anti-inflammatory effect are for example 0.1 to 600 mg, preferably 15 to 400 mg and in particular 50 to 200 mg of dihydrolipoic acid.

The direction of the effect of dihydrolipoic acid is comparable to the effect of the known active substances alpha-lipoic acid and S-adenosyl-L-methionine, although the following differences exist in particular:

1. The full effect appears in animal experiments only 0.5 hours after application and not, as is the case with S-adenoxyl-L-methionine, after repeated administration.
2. The effect of dihydrolipoic acid is for example stronger than that of alpha-lipoic acid by a factor of 2-3.

In accordance with the invention a daily dose of dihydrolipoic acid of 10-600 mg, for example 25 to 400 mg or 10 to 200 mg is administered. The maximum daily dose should not exceed 600 mg. The daily doses may be given in the form of a single administration of the entire amount or in the form of 1 to 6, in particular 1 to 4 partial doses per day. In particular, administration 1 to 4 times, in particular 1 to 3 times daily is preferred. For example the preferred daily dose of the dihydrolipoic acid is preferably 80 mg for the parenteral form of application and 200 mg for the oral form. In particular the daily dose for the parenteral form of application is 50 mg and 150 mg for the oral form.

Preferably, the pharmaceutical composition is administered orally.

The dihydrolipoic acid may in particular also be applied in the form of a solution, application preferably being peroral, topical, parenteral (intravenous, intra-articular, intramuscular, subcutaneous), by inhalation, rectal, transdermal or vaginal.

The compositions which contain the dihydrolipoic acid as active substance can, for example, be formulated in the form of tablets, capsules, pills or coated tablets, granulates, suppositories, pellets, plasters, solutions or emulsions, the active substance being combined with appropriate auxiliary and carrier substances. In the case of solutions, these contain for example 0.5 to 20 % by weight, preferably 1 to 10 % by weight of dihydrolipoic acid.

The dosage unit of the pharmaceutical composition containing the dihydrolipoic acid or a therapeutically acceptable salt thereof may for example contain:

a) in the case of peroral medicinal forms:
10 to 600 mg, preferably 20 to 400 mg, in particular 50 to 200 mg of dihydrolipoic acid.
The doses may for example be administered 1 to 6, preferably 1 to 4, in particular 1 to 3 times daily. However a total dose of 600 mg per day should not be exceeded. The same also applies for the following medicinal forms listed under b) to e).

b) in the case of parenteral medicinal forms (for example intravenous, intramuscular or intra-articular):
10 to 300 mg, preferably 15 to 200 mg, in particular 20 to 100 mg of dihydrolipoic acid.
The doses may for example be administered 1 to 6, preferably 1 to 4, in particular 1 to 3 times daily.

c) In the case of medicinal forms for rectal or vaginal application:
10 to 500 mg, preferably 40 to 400, in particular 50 to 200 mg of dihydrolipoic acid.
The doses may for example be given 1 to 6, preferably 1 to 4, in particular 1 to 3 times daily.

d) In the case of medicinal forms for application to the skin and mucous membranes (for example as solutions, lotions, emulsions, ointments, plasters and the like): 10 to 500 mg of dihydrolipoic acid, preferably 40 to 250 mg, in particular 50 to 200 mg of dihydrolipoic acid.
The doses may for example be given 1 to 6, preferably 1 to 4, in particular 1 to 3 times daily.

e) In the case of medicinal forms for inhalation (solutions or aerosols):
0.1 to 300 mg, preferably 0.25 to 150 mg, in particular 0.5 to 80 mg of dihydrolipoic acid.
The doses may for example be given 1 to 6, preferably 1 to 4, in particular 1 to 3 times daily.

Should lotions be used, the dihydrolipoic acid is preferably used in the form of a salt.

It is of course also possible to prepare pharmaceutical formulations which contain the above mentioned dosage units 2 to for example 6 times. In particular tablets or capsules contain 20 to 500 mg; pellets, powders or granulates 20 to 400 mg, suppositories 20 to 300 mg of dihydrolipoic acid.

The acute toxicity of the invention in the mouse (expressed as the $LD_{50}$ mg/kg; method of LITCHFIELD and WILCOXON, J. Pharmacol. Exp. Ther. 95:99, (1949)) is for example above 200 mg/kg in the case of oral application.

The dosages set out above relate in each case to free dihydrolipoic acid. Should dihydrolipoic acid be used in the form of a salt, the dosages and dosage ranges given must be increased accordingly as a result of the higher molecular weight.

Should the dihydrolipoic acid be used in animals, the following indications may be considered in particular: hepatoses, Arthrosis deformans, arthritis and dermatitis. Examples for the treatment of animals:

For the treatment of dogs and cats the single oral dose is generally between about 2 mg/kg and 50 mg/kg body weight, the parenteral dose is between about 0.5 and 40 mg/kg body weight.

For the treatment of arthroses in horses and cattle the oral single dose is generally between about 2 mg/kg and 100 mg/kg body weight, the parenteral dose between about 0.5 and 50 mg/kg body weight.

Dihydrolipoic acid is suitable for the preparation of pharmaceutical compositions and formulations. The pharmaceutical compositions and formulations contain dihydrolipoic acid as active substance, optionally mixed with other pharmacologically or pharmaceutically active substances. The pharmaceutical compositions are prepared in the conventional manner, using conventional and customary pharmaceutical auxiliary substances as well as other conventional carriers and diluents. Carriers and auxiliary substances which may for example be used are those substances which are recommended or cited in the following literature references as being auxiliary substances for the pharmaceutical, cosmetic and related fields: Ullmanns Encyklopädie der technischen Chemie, Volume 4 (1953), page 1 to 39; Journal of Pharmaceutical Sciences, Volume 52 (1963), page 918 et seq., H.v. Czetsch-Lindenwald, Hilfsstoffe für Pharmazie und angrenzende Gebiete; Pharm. Ind., Issue 2, 1961, page 72 et seq; Dr. H.P. Fiedler, Lexikon der Hilfsstoffe für Pharmazie, Kosmetik und angrenzende Gebiete Cantor KG. Aulendorf in Württemberg 1981.

Examples thereof are gelatins, natural sugars such as cane sugar or lactose, lecithin, pectin, starches (for example corn starch or amylose), cyclodextrins and cyclodextrin derivatives, dextran, polyvinylpyrrolidone, polyvinylacetate, gum arabic, alginic acid, tylose, talcum, lycopodium, silicic acid (for example colloidal), cellulose, cellulose derivatives (for example cellulose ethers in which the cellulose hydroxy groups are partially etherified with lower saturated aliphatic alcohols and/or lower saturated aliphatic oxyalcohols, for example methyloxypropyl cellulose, methyl cellulose, hydroxypropyl methyl cellulose, hydroxypropyl methyl cellulose phthalate); fatty acids as well as magnesium, calcium or aluminum salts of fatty acids having 12 to 22 carbon atoms, in particular saturated ones (for example stearates), emulsifiers, oils and fats, in particular vegetable (for example peanut oil, castor oil, olive oil, sesame oil, cottonseed oil, corn oil, wheat germ oil, sunflower seed oil, cod liver oil, in each case also hydrated); glycerin esters and polyglycerin esters of saturated fatty acids $C_{12}H_{24}O_2$ to $C_{18}H_{36}O_2$ and their mixtures, where the glycerin hydroxy groups are wholly or also only partially esterified (for example mono-, di- and triglycerides); pharmaceutically acceptable mono- or multivalent alcohols and polyglycols such as polyethylene glycols as well as derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerine, diethylene glycol, pentaerythritol, sorbitol, mannitol and so on, which may optionally also be etherified, esters of citric acid with primary alcohols, acetic acid, urea, benzyl benzoate, dioxolanes, glycerine formals, tetrahydrofurfuryl alcohol, polyglycol ethers with $C_1$-$C_{12}$ alcohols, dimethylacetamine, lactamides, lactates, ethyl carbonates, silicons (in particular medium-viscous polydimethylsiloxanes), calcium carbonate, sodium carbonate, calcium phosphate, sodium phosphate, magnesium carbonate and the like.

Other auxiliary substances may also be substances which effect disintegration (so-called disintegrants) such as: cross-linked polyvinylpyrrolidone, sodium carboxymethyl starch, sodium carboxymethyl cellulose or microcrystalline cellulose. It is also possible to use conventional coating substances. Those which may for example be used are: polymerizates as well as copolymerizates of acrylic acid and/or methacrylic acid and/or their esters; copolymerizates of acrylic and methacrylic acid esters with a low ammonium group content (for example Eudragit ® RS), copolymerizates of acrylic and methacrylic acid esters and trimethyl ammonium methacrylate (for example Eudragit ® RL); polyvinylacetate; fats, oils, waxes, fatty alcohols; hydroxypropyl methyl cellulose phthalate or acetate-succinate; cellulose acetate phthalate starch-acetate phthalate as well as polyvinyl acetate phthalate; carboxymethyl cellulose; methyl cellulose phthalate, methyl cellulose succinate, -phthalate succinate as well as methyl cellulose phthalate acid half ester; zein, ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethylhexyl-acrylate maleic acid anhydride; crotonic acid-vinyl acetate copolymer; glutaminic acid/glutaminic acid ester copolymer; carboxymethyl ethyl-cellulose glycerine monooctanoate; celluloseacetate succinate; polyarginin.

Plasticizing agents for coating substances that may be used are:

Citric and tartaric acid esters (acetyltriethyl citrate, acetyltributyl-, tributyl-, triethyl-citrate); glycerin and glycerin esters (glycerine diacetate, triacetate, acetylated monoglycerides, castor oil); phthalic acid esters (dibutyl-, diamyl-, diethyl-, dimethyl-, dipropyl phthalate), di-(2-methoxy- or 2-ethoxyethyl)phthalate, ethylphthalyl glycolate, butylphthalyl ethyl glycolate and butylglycolate; alcohols (propylene glycol, polyethylene glycol of various chain lengths), adipates (diethyl adipate, di-(2-methoxy or 2-ethoxy ethyl)-adipate), benzophenone; diethyl- and dibutyl sebacate, dibutyl succinate, dibutyl tartrate; diethylene glycol diproprionate; ethylene glycol diacetate, - dibutyrate, -dipropionate; tributyl phosphate, tributyrin; polyethylene glycol sorbitan monooleate (polysorbates such as polysorbate 80); sorbitan monooleate.

To prepare solutions or suspensions, it is for example possible to use water or physiologically acceptable organic solvents such as ethanol, propanol, isopropanol, 1,2-propylene glycol, polyglycols and their derivatives, dimethylsulphoxide, fatty alcohols, triglycerides, partial esters of glycerine, paraffins and similar. Polyethylene glycols which may for example be used are those with molecular weights between 100 and 6000, preferably 200 to 4000.

In the case of injectable solutions or suspensions it is for example possible to use non-toxic parenterally acceptable diluents or solvents, such as for example: water, 1,3-butane diol, ethanol, 1,2-propylene glycol, polyglycols mixed with water, glycerol, Ringer's solution, isotonic sodium chloride solution, natural oils (for example peanut oil, olive oil, sesame oil, almond oil, sunflower oil, soya bean oil, castor oil, ox-foot oil) or also hardened oils including synthetic mono or diglycerides or fatty acids such as oleic acid.

Formulations may be prepared using known and conventional diluents or emulsifiers. Diluents and emulsifiers which may for example be considered are: nicotinic acid amide, polyvinylpyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context the term polyoxyethylated means that the substances in question contain polyoxyethylene chains, the degree of polymerization of which generally lies between 2 to 40 and in particular between 10 to 20.

Polyoxyethylated substances of this type may for example be obtained through reaction of hydroxyl group containing compounds (for example mono or diglycerides or unsaturated compounds such as for example those which contain oleic acid radicals) with ethylene oxide (for example 40 Mol of ethylene oxide per 1 Mol of glyceride).

Examples of oleotriglycerides are olive oil, peanut oil, castor oil, sesame oil, cotton seed oil, corn oil.

See also Dr. H.P. Fiedler "Lexikon der Hilfsstoffe für Pharmazie, Kosmetik und angrenzende Gebiete" 1971, p. 191-195.

It is also possible to add preservatives, stabilizers, buffer substances, flavor correcting agents, sweeteners, colorants, antioxidants, complex formers and the like.

Complex formers which may for example be used are: chelate formers such as ethylene diamino tetraacetic acid, nitrilotriacetic acid, diethylenetriamino pentaacetic acid and their salts.

The complex formers may also be those which contain dihydrolipoic acid in a pore space. Examples are urea, thiourea, cyclodextrines and amylose.

It is optionally possible to stabilize the active substance molecule to a pH of ca. 6 to 9 using physiologically acceptable bases or buffers. Generally speaking, as neutral or weakly basic (up to pH 8) a pH value as possible is preferred.

Antioxidants which may for example be used are sodium sulfite, sodium hydrogen sulfite, sodium metabisulfite, ascorbic acid, ascorbyl palmitate, -myristate, -stearate, gallic acid, gallic acid alkyl ester, butylhydroxyanisol, nordihydroguaiacic acid, tocopherols as well as synergists (substances which bind heavy metals through complex formation, for example lecithin, ascorbic acid, phosphoric acid, ethylenediaminotetraacetic acid, citrate, tartrate). The addition of synergists substantially increases the antioxygenic effect of the antioxidants. Preservatives which may for example be considered are sorbic acid, p-hydroxybenzoic acid esters (for example lower alkyl esters), benzoic acid, sodium benzoate, trichloroisobutyl alcohol, phenol, cresol, benzethonium chloride, chlorohexidine and formalin derivatives.

The pharmaceutical and galenic treatment of dihydrolipoic acid is effected using conventional standard methods. For example the dihydrolipoic acid and auxiliary or carrier substances are well mixed by stirring or homogenizing (for example using conventional mixing devices), working generally being at temperatures between 20° and 80° C., preferably 20° to 50° C., in particular at room temperature. Reference is also made to the following standard work: Sucker, Fuchs, Speiser, Pharmazeutische Technologie, Thieme-Verlag Stuttgart, 1978.

The dihydrolipoic acid or the pharmaceutical composition may be applied to the skin or mucous membrane or to the inside of the body, for example by the oral, enteral, pulmonary, rectal, nasal, vaginal, lingual, intravenous, intra-arterial, intracardial, intramuscular, intraperitoneal, intracutaneous, subcutaneous route.

The parenteral formulations are in particular sterile or sterilized products.

The dihydrolipoic acid may also be used or employed in the form of its salts, it also being possible to use the salt former in excess, i.e. in a higher amount than equimolar.

Salt formers for dihydrolipoic acid may for example be the conventional bases or cations which are physiologically acceptable in the salt form. Examples are: acceptable alkaline or alkaline earth metals, ammonium hydroxide, basic amino acids such as arginine and lysine, amines of the formula $NR_1R_2R_3$ wherein the radicals $R_1$, $R_2$ and $R_3$ are the same or different and represent hydrogen, $C_1-C_4$ alkyl or $C_1-C_4$ oxyalkyl such as mono and diethanolamine, 1-amino-2-propanol, 3-amino-1-propanol; alkylenediamines having an alkylene chain composed of 2 to 6 carbon atoms, such as ethylene diamine or hexamethylentetramine, saturated cyclic amino compounds having from 4 to 6 carbon atoms in the ring, such as piperidine, piperazine, pyrrolidone, morpholine; N-methylglucamine, creatine, tromethamine.

The following is a brief description of the pharmacological test methods specially mentioned herein: *Randall Selitto Test* (inflammatory pain in the rat):

On the basis of the method after RANDALL and SELITTO (L.O. Randall and J. Selitto, Arch. int. Pharmacodyn., Vol. 111, pages 409-418 (1957)) 0.1 ml of a 20% suspension of brewer's yeast (in demineralized water) is injected subplantar into the right rear paw of rats. After 2½ hours the test substances are given and 30 minutes later the pain threshold is measured as a pressure (in grams) on the inflamed paw using an algesimeter (equipment by Ugo BASILE, Milan/Italy). The criterion is the defense reaction of the animals in pulling the paw away and/or escaping from the technician's grip. The effect of the substance is determined by the increase in the pain threshold compared to an untreated control group. The course of the experiment differs from the original method in that the substances are only administered 2½ hours after appearance of the edema and not given simultaneously therewith. This is done in order to prevent the development of the edema being inhibited by any possible anti-inflammatory action and the analgesia being masked or feigned.

The $ED_{50}$ is determined using the linear regression method. The $ED_{50}$ is then the dose in mg/kg for which a 50% analgesic effect is calculated.

Acetic acid test (Writhing test) in the mouse

Method

In the acetic acid test after KOSTER et al. (Fed. proc., Vol. 18, page 412 (1959)) the pain irritation is triggered by an intraperitoneal injection of 1% acetic acid. The pain reaction is expressed in the form of a characteristic stretching of the animals ("writhing syndrome") which continues at irregular intervals for some time after the acetic acid injection. The dose-related inhibition of the frequency of writhing movements as compared to an untreated control group is expressed as an analgesic effect in percent. Evaluation is effected by determining the $ED_{50}$ (linear regression method). The $ED_{50}$ is the dose in mg/kg which achieves a 50% inhibition in the writhing syndrome.

The characteristic feature of the acetic acid test is that it not only determines the effect of strong, centrally acting analgesics, but also that of predominantly peripherally acting analgesic, antipyretic and anti-inflammatory agents such as phenylbutazone, indomethacin, etc. The effect in this experiment therefore suggests that the analgesia has a peripheral component.

Carragheen-edema test for anti-inflammatory effect

The examination is carried out in carragheen-induced edema of rat paw on the basis of the method of MöRSDORF and colleagues (Arch. int. Pharmacodyn. 192, 111-127 (1971)). The anti-inflammatory effect is for example quoted as edema inhibition in percent as compared to the untreated control group. In all experiments application is oral. The substance is given orally or intraperitoneally 1 hour after triggering of the infection. The $ED_{50}$ is the dose in mg/kg at which there is a 50% inhibition of the paw edema.

Investigations in PAF (Platelet Aggregating Factor)-acether-edema in the rat

The principle of this method is to provoke a locally limited edema or inflammation in the rat paw by means of the subplantar injection of 2 μg of PAF acether per animal. The investigations were carried out on the basis of the method of SWINGLE and REITER (Agents and actions, 18, 358–365, (1986)). The animals received the test substances 0.5 hours before triggering of the edema. The edema was measured 1 hour thereafter. The $ED_{50}$ was calculated using the linear regression method.

DETAILED DESCRIPTION OF PREFERRED EMBODIMENTS

The following examples illustrate the invention:

Example 1

Ampoules containing 250 mg of dihydrolipoic acid in 10 ml injection solution:

60 g of tromethamine and 1 g of ethylene diamine tetraacetic acid disodium salt are dissolved in 1.8 liters of water for injection purposes. The solution is gassed for 30 minutes using nitrogen. 2 g of sodium disulfite and then 50 g of dihydrolipoic acid are dissolved in the mixture while gassing with nitrogen continues. The solution is diluted to a volume of 2 liters using sterile water that has been gassed with nitrogen. After careful mixing the solution is filtered through a membrane filter of pore size 0.2 μm and the filtrate filled into ampoules in batches of 10 ml under aseptic conditions and with pre and post gassing with nitrogen into ampoules having a volume of 10 ml.

Each ampoule contains 250 mg of dihydrolipoic acid as tromethamine salt in 10 ml of solution.

Example 2

Suppositories containing 200 mg of dihydrolipoic acid 5 g of ascorbylpalmitate and 5 g of Oxynex LM[1] (E. Merck, Darmstadt) are suspended in 180 g of melted hard fat.[2] 20 g of dihydrolipoic acid are then mixed therewith and the mixture is poured, after homogenizing, into 2.3 ml hollow cells and allowed to cool. The hollow cells are flushed with nitrogen before being closed. *

[1] Oxynex LM is a commercially available additive for fats and fat-containing foodstuffs. It is a pale brown to brown, waxy mass which melts on heating to 55° C. to a clear brown fluid and contains -tocopherol, ascorbylpalmitate, citric acid and lecithin. *
[2] Hard fat is a mixture of mono-, di- and triglycerides of saturated fatty acids of $C_{10}H_{20}O_2$ to $C_{18}H_{36}O_2$.

Each suppository weighing 2.1 g contains 200 mg of dihydrolipoic acid.

Example 3

Cream containing 10% dihydrolipoic acid 50 g of polyoxyethylene-40-stearate (trade name: Myrj$^R$52), 80 g of cetylstearyl alcohol, 200 g of white Vaseline, 50 g of highly viscous paraffin and 5 g of dimethicone are melted together in a homogenizing apparatus. 1.26 g of methyl-4-hydroxybenzoate and 0.533 g of propyl-4-hydroxybenzoate are dissolved into the melt.

1.4 g of methyl-4-hydroxybenzoate and 0.6 g of propyl-4-hydroxybenzoate are dissolved in 511.207 g at 70° C. The solution is emulsified into the fat melt obtained as above. The emulsion is homogenized and cooled to room temperature with stirring. 100 g of dihydrolipoic acid are then stirred into the cream and the cream is homogenized once more under a vacuum.

What is claimed is:

1. A method of treating an inflammatory disease comprising administering, to a patient having an inflammatory disease, an effective anti-inflammatory amount of dihydrolipoic acid or a pharmaceutically acceptable salt thereof.

2. A method as set forth in claim 1 in which the disease which is treated is selected from inflammatory, degenerative articular and extra-articular rheumatic disorders, non-rheumatic inflammatory and swollen states, Arthrosis deformans, chrondropathies, periarthritis, inflammatory disorders of the skin, inflammatory disorders of the gastrointestinal tract, polyneuropathy of diabetic, alcoholic, hepatic and uraemic origin, liver parenchyme degeneration, hepatitis, fatty liver and fatty cirrhosis, chronic liver disorders and inflammatory respiratory tract disorders.

* * * * *